United States Patent
Lihl et al.

(10) Patent No.: US 7,080,583 B2
(45) Date of Patent: Jul. 25, 2006

(54) METHOD AND APPARATUS FOR PRESETTING SPECIMENS IN A CUTTING DEVICE

(75) Inventors: Reinhard Lihl, Vienna (AT); Hubert Goll, St. Poelten (AT); Anton Lang, Vienna (AT); Paul Wurzinger, Deutsch-Wagram (AT)

(73) Assignee: Leica Microsysteme GmbH, Vienna (AT)

( * ) Notice: Subject to any disclaimer, the term of this patent is extended or adjusted under 35 U.S.C. 154(b) by 174 days.

(21) Appl. No.: 10/735,397

(22) Filed: Dec. 12, 2003

(65) Prior Publication Data
US 2004/0178371 A1    Sep. 16, 2004

(30) Foreign Application Priority Data
Dec. 14, 2002  (DE) ................. 102 58 555

(51) Int. Cl.
  *B26D 1/00*    (2006.01)

(52) U.S. Cl. .................... 83/13; 83/522.16; 83/522.22; 83/915.5; 250/221; 250/559.12

(58) Field of Classification Search .................... 83/13, 83/520, 915.5, 521, 522.22, 522.16, 575, 83/34, 75, 368, 76.8; 250/559.12, 221, 458.1; 422/82.08; 409/293, 289
See application file for complete search history.

(56) References Cited

U.S. PATENT DOCUMENTS

| | | | | |
|---|---|---|---|---|
| 3,690,154 A | * | 9/1972 | Wells et al. ................... 73/615 |
| 3,845,659 A | * | 11/1974 | Wikefeldt et al. ........ 73/862.06 |
| 4,426,179 A | * | 1/1984 | Jefferson ...................... 409/82 |
| 4,856,326 A | * | 8/1989 | Tsukamoto ............... 73/150 A |
| 5,119,759 A | * | 6/1992 | Hicks .......................... 118/712 |
| 5,282,404 A | * | 2/1994 | Leighton et al. ................ 83/13 |
| 5,533,342 A | * | 7/1996 | Gordon ...................... 62/51.1 |
| 5,535,654 A | * | 7/1996 | Niesporek et al. ............. 83/364 |
| 5,609,083 A | * | 3/1997 | Persson ......................... 83/14 |
| 5,671,648 A | * | 9/1997 | Dern ......................... 83/411.1 |
| 6,568,307 B1 | * | 5/2003 | Günther et al. ............... 83/367 |
| 6,634,268 B1 | * | 10/2003 | Guenther et al. ............... 83/13 |

FOREIGN PATENT DOCUMENTS

| | | |
|---|---|---|
| DE | 3615715 | 11/1988 |
| DE | 4111689 | 10/1991 |
| EP | 0544181 | 6/1993 |

* cited by examiner

*Primary Examiner*—Allan N. Shoap
*Assistant Examiner*—Ghassem Alie
(74) *Attorney, Agent, or Firm*—Simpson & Simpson, PLLC

(57) ABSTRACT

In microtomes or ultramicrotomes, it is necessary to preset the specimen (14) onto the knife (16). In order to facilitate and automate this presetting operation, which is intended to guarantee the fastest and most accurate possible positioning of the knife (16) relative to the specimen (14), the spacing (13) between the trimmed surface (15) of the specimen (14) and the specimen holder (22) is ascertained and is transferred to the microtome or ultramicrotome (10). The spacing (13) is preferably ascertained in the trimming device (12).

6 Claims, 3 Drawing Sheets

METHOD AND APPARATUS FOR PRESETTING SPECIMENS IN A CUTTING DEVICE

CROSS REFERENCE TO RELATED APPLICATIONS

This application claims priority of the German patent application 102 58 555.5-52, filed on Dec. 14, 2002, which is incorporated by reference herein.

FIELD OF THE INVENTION

The invention concerns a method for cutting a specimen having a trimmed surface with a microtome or ultramicrotome. The invention concerns as well a microtome or ultramicrotome for cutting a specimen. Additionally, the invention concerns a system for automatically presetting a specimen onto a knife in a microtome or ultramicrotome.

BACKGROUND OF THE INVENTION

For the optical examination of specimens, thin sections of the specimens are often produced and are then examined with a microscope, for example a light or electron microscope. In the case of biological specimens in particular, it is often advantageous to embed them in a plastic in order to immobilize them sufficiently. For production of a thin section of the specimen, the specimen must then be exposed at the desired cut surface. This can be accomplished, for example, manually using a razor blade. While this method requires little technical complexity, it is nevertheless often not possible to trim the specimen exactly enough. In particular, flat cut surfaces cannot be generated.

A trimming apparatus is therefore used for exact trimming. For this purpose, the specimen with its plastic sheathing is clamped in a specimen holder. The specimen holder is then secured in the trimming apparatus. A motor-driven milling cutter then removes material under observation through a stereomicroscope, until a milled surface of the specimen is exposed at the location to be examined.

After milling, the thin or ultra-thin sections of the specimen can be produced. For this, the specimen mount together with the specimen is secured in a cutting device, for example the microtome or ultramicrotome. The specimen to be cut must then be exactly positioned in the cutting device with respect to the knife in accurately positioned and rapid fashion. Care must be taken that neither the knife nor the specimen is damaged in this so-called "presetting" operation. It is correspondingly necessary to prevent inadvertent contact from occurring between knife and specimen.

It has therefore been common for some time, in the context of the presetting operation between knife and specimen, to observe through a stereomicroscope as the knife and specimen approach one another. This observation does not always, however, result in a reliable estimate of the spacing between the specimen and the knife edge. Technical presetting aids have therefore also been used for some time, for example a base-mounted illumination system; with this it is possible to illuminate a gap between the knife and specimen, and on the basis of the illuminated gap to allow a better evaluation of the spacing between specimen and knife. A light source below the knife allows the spacing between knife and specimen to appear as a bright gap. An approach to within a few micrometers is required so that in the context of a diamond knife, which permits a maximum cut thickness of approx. 0.3 µm, it is not necessary to wait too long for the first cut.

This accuracy is also necessary for adjustment of the knife swing and specimen swing, since if an angular error exists, the first cuts result only in fragments of the entire trimmed surface. This procedure during presetting requires a great deal of practice on the part of the user in question, and is moreover extremely time-consuming.

It is already known from DE 41 11 689 to provide a force sensor that is mounted on the specimen or knife. The cutting force is sensed with the aid of this force sensor, so that it is possible to ascertain when the first cut occurs. In order to carry out the method, once an initial coarse positioning of the knife with respect to the specimen has been performed, the spacing between specimen and knife is decreased at a high feed and cutting speed. As soon as the specimen touches the knife for the first time, the force sensor responds. From that time on, operation switches to a selectable (usually slower) cutting speed, and a specific desired cut thickness is maintained.

In order to minimize stress on the specimen and knife, however, the first cuts after presetting must also not be too thick. For many diamond knives, a cut thickness of 0.3 µm is considered the upper limit. This means that before cutting operation begins, alignment of the knife and specimen must be accomplished to an accuracy of a few micrometers without contact between the knife and specimen. The method proposed in DE 41 11 689 cannot guarantee this, however. The first contact between knife and specimen takes place at high speed, so that damage to the knife and specimen can thereby occur.

In order to improve the presetting operation and to automate presetting, with the intent of simultaneously avoiding uncontrolled contact between the knife and specimen, EP 544 181 has proposed a method and an apparatus for automatic presetting. For this, there is mounted on the knife holder a so-called limiting device which is provided in order automatically to ascertain the proximity of the specimen holder along with the specimen secured therein. At the same time, the drive device is intended to switch off in timely fashion so that damage to the knife blade and to the specimen is reliably prevented. To ensure this, a movable plate having a microswitch located behind it is provided on the knife holder. In the presetting operation, the specimen is moved toward this plate until the switching point of the microswitch is reached. A disadvantage of this method, however, is the fact that contact between the specimen and the plate is necessary. In addition, the microswitch does not have the requisite repeatability in the micrometer range.

SUMMARY OF THE INVENTION

It is therefore the object of the present invention to propose a method for cutting a specimen with a trimmed surface which allows rapid and non-contact presetting and thereby being user friendly.

According to the present invention, this object is achieved by a method comprising the steps of:

providing a knife holder for a knife and a specimen holder for holding the specimen, using a feed device for producing a relative motion between the knife and the specimen, the specimen, ascertaining in a trimming apparatus the spacing between the trimmed surface of the specimen and the specimen holder, transferring the spacing to the cutting device, and inserting the specimen holder into the cutting device.

A further object of the invention is to propose a microtome or ultramicrotome for cutting a specimen and allowing rapid presetting and user friendliness.

The above object is achieved by a microtome or ultramicrotome comprising: a knife holder for a knife and a specimen holder for holding the specimen, a feed device for producing a relative motion between the knife and the specimen and a travel measurement system for measuring the change in the spacing between the knife and the specimen holder.

It is a further object of the invention to provide a system which allows automatic presetting of system parameters.

The object is achieved by a system for automatically presetting a specimen onto a knife in a microtome or ultramicrotome. The system comprising: a travel measurement system for measuring the change in the spacing between the knife and the specimen holder, a device for transmitting the distance, ascertained in a trimming device, between a trimmed surface of the specimen and the specimen holder, and the trimming device is coupled to the cutting device in such a way that the spacing ascertained in the trimming device is transmitted to the microtome or ultramicrotome.

The method and the apparatus according to the present invention thus create a capability for decreasing and automating the time for presetting a specimen onto a knife in a cutting device. At the same time, they ensure that neither the specimen nor the knife sustains damage during presetting. In terms of the method, therefore, the spacing between the trimmed surface of the specimen and the specimen holder is ascertained in a first step. That ascertained spacing is then transferred to the cutting device. When the knife and the specimen in the cutting device are then inserted in defined fashion, their spacing is known.

With the transfer of the spacing between the specimen holder and the trimmed surface of the specimen, it is easy to calculate the amount by which the relative distance between the specimen and the knife in the cutting device must be modified until the knife has reached its preset position with respect to the specimen.

Advantageously, the spacing between the specimen holder and the trimmed surface of the specimen in the trimming device is ascertained during trimming of the specimen. For this purpose, the trimming device is equipped with a distance measurement system. The spacing of the trimming knife from the specimen holder without an inserted specimen is determined once, and stored. The position of the trimming knife before trimming begins is sensed as the so-called zero position. A specimen is inserted into the specimen holder and the trimming operation can be started, the trimming knife usually being moved toward the specimen. The distance traveled is sensed with the aid of a distance measurement system. As soon as trimming of the specimen is complete, the distance traveled by the trimming knife is also known. From the difference between the distance traveled and the known distance between the zero position of the trimming knife and the specimen holder, it is possible to ascertain the spacing between the cut surface of the specimen and the specimen holder.

The specimen holder with the trimmed specimen is thus inserted into a cutting device, in particular a microtome or ultramicrotome, in a defined position. The data previously ascertained, in particular in the trimming device, are transmitted to the cutting device e.g. via an interface. Automatic presetting of the knife onto the specimen can thus be accomplished in the cutting device.

In order for the method according to the present invention to be accomplished, a capability therefore must be created for ascertaining the distance between the trimmed surface of the specimen and the specimen holder, and for transferring the acquired data to the cutting device. A distance measurement system is thus provided in the trimming device and in the cutting device. A device for transmitting the data, in particular an interface, is furthermore provided in the cutting device. The interface can be supplied with data by way of data cables or in wireless fashion.

According to the present invention, the trimming device and the cutting device can constitute a system for automatically presetting a specimen in the cutting device, in which context the spacing between the specimen holder and the trimmed surface of the specimen is ascertained in the trimming device. That information is transmitted to the cutting device, so that an automatic presetting operation can be performed in the cutting device.

BRIEF DESCRIPTION OF THE DRAWINGS

Further advantages and advantageous embodiments of the invention are the subject matter of the Figures below and the descriptions thereof.

In the individual Figures.

DETAILED DESCRIPTION OF THE INVENTION

Figure 1:
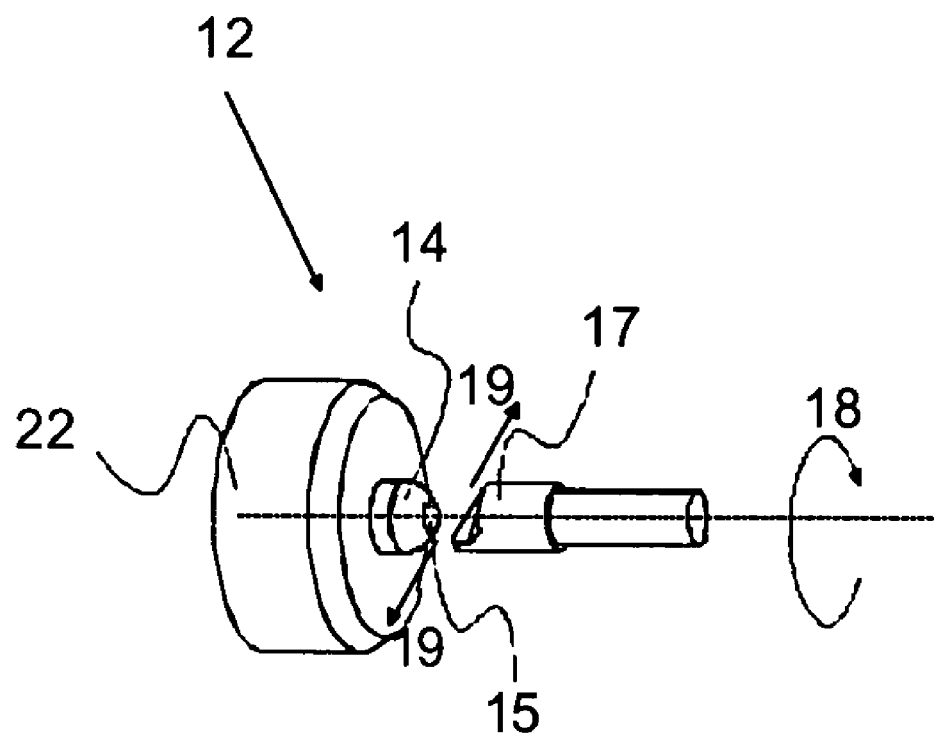
FIG. 1 is a schematic depiction of a trimming device.

FIG. 1 schematically depicts a trimming device 12. A specimen 14 is clamped in a specimen holder 22. Depending on the intended further examination and the nature of the specimen, the desired upper surface is produced on surface 15 of specimen 14 facing toward the trimming knife or milling cutter 17, the selected specimen surface being centered and milled flat in the shape of a block using milling cutter 17. Milling cutter 17 is rotated in rotation direction 18 for this purpose. In order to generate the desired surface 15 of specimen 14, the milling cutter can be displaced in direction 19. According to the present invention, trimming device 12 is equipped with a distance measurement system that permits a determination of the spacing between trimmed surface 15 and specimen holder 22. The spacing of milling cutter 17 from specimen holder 22 without an inserted specimen 14 is determined once, and stored. The position of milling cutter 17 before trimming begins is sensed as the so-called zero position. A specimen 14 is then inserted into specimen holder 22 and the trimming operation is begun. In this, milling cutter 17 is moved toward specimen 14 and the distance traveled is sensed by way of the distance measurement system. After the trimming of specimen 14 ends, the distance traveled by milling cutter 17 is also known. From the difference between the distance traveled and the known distance between the zero position of milling cutter 17 and specimen holder 22, the spacing between cut surface 15 of specimen 14 and specimen holder 22 can be ascertained. To simplify the determination of the spacing, trimming device 12 can be controlled in such a way that it automatically moves to the zero position at each activation.

Figure 2:
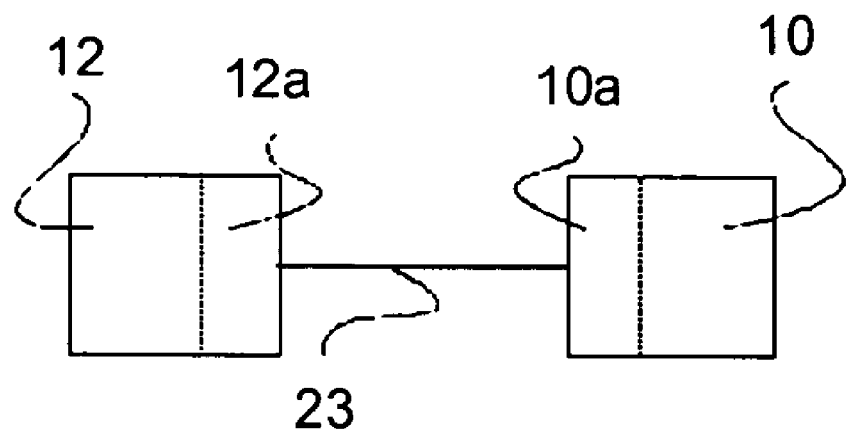
FIG. 2 schematically depicts the transmission of data.

As shown in FIG. 2, the data thus obtained are transferred from trimming device 12 via a data transfer means 23 to cutting device 10. Data transmission units 10*a*, 12*a* can be provided in this context both in trimming device 12 and in cutting device 10. These units are usually embodied as interfaces, and make possible the transfer of data using data transfer means 23. The data transfer means can be embodied as a data line, in particular as a ribbon cable, or as a wireless communication device, in particular as IR waves.

Figure 3:
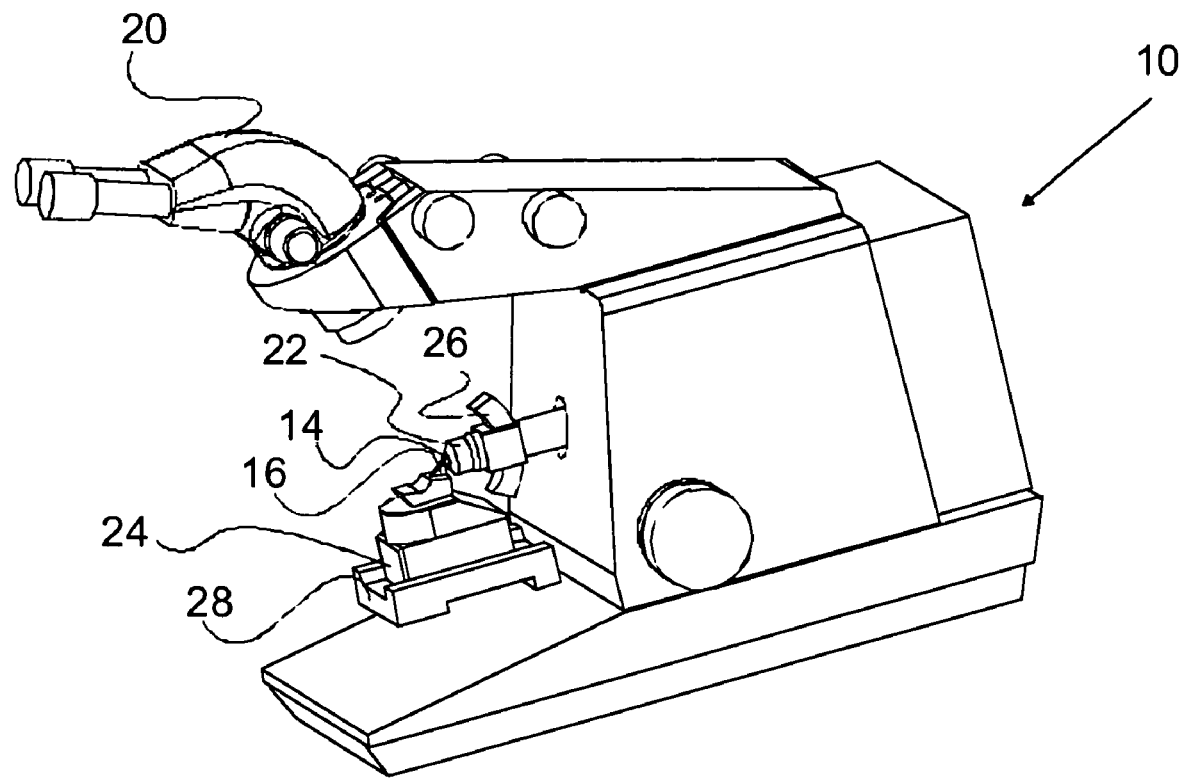
FIG. 3 is an overall view of a cutting device according to the present invention.

FIG. 3 shows a general view of a cutting device 10. It comprises a stereomicroscope 20 with which the cutting operation can be observed. The milled specimen 14 is inserted, with specimen holder 22, into a swing arm 26 in a defined position. A knife 16 that is secured on a rotatably mounted knife holder 24 is provided for cutting. The arrangement can be displaced with the aid of translationally movable X-Y stage 28. A distance measurement system for measuring the travel of the X-Y stage is also provided.

Figure 4:
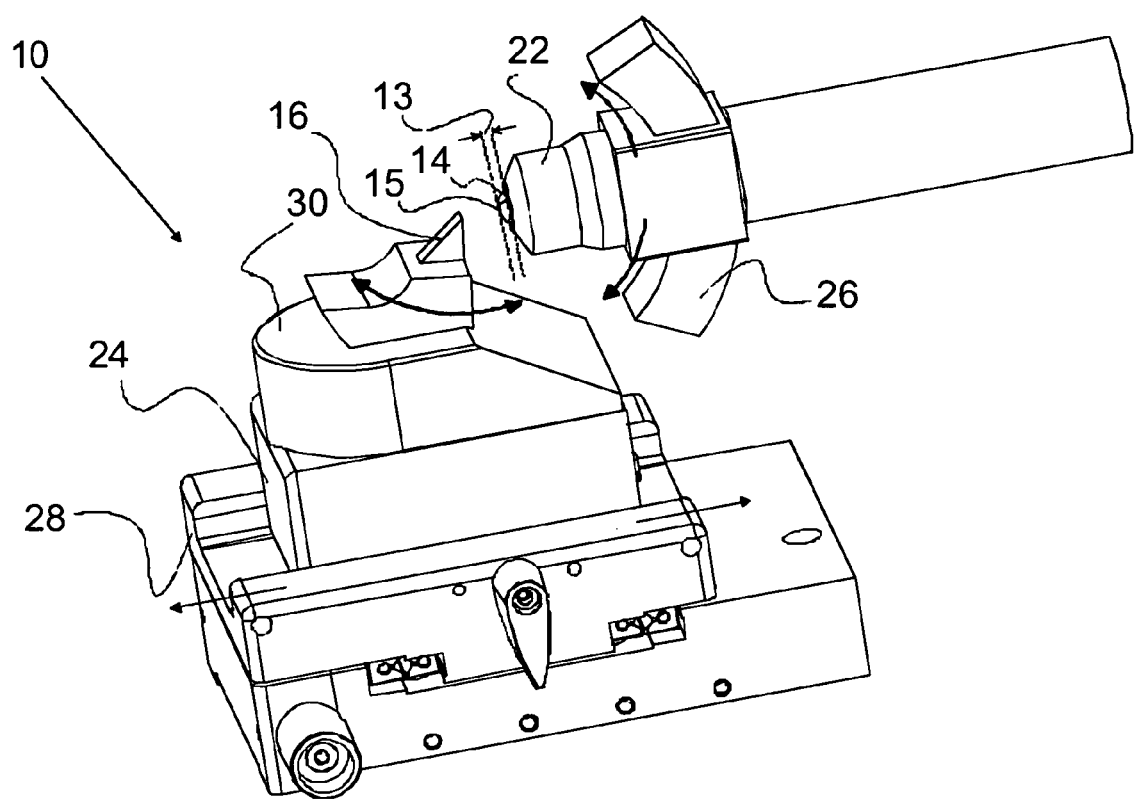
FIG. 4 shows a portion of a cutting device according to the present invention.

FIG. 4 depicts an magnified portion of cutting device 10. After trimming, specimen 14 is secured in cutting device 10, together with specimen holder 22, until it comes to a stop. Knife holder 24 is slid into X-Y stage 28 until it stops, and clamped so that an immovable connection exists between knife holder 24 and X-Y stage 28. Knife swing 30 is set to 0°. At the same time, the swinging motion of specimen 14 using swing arm 26 is omitted, or it is likewise set to 0°. The measurement data ascertained in the trimming apparatus are transmitted, as described above, to cutting device 10. The automatic presetting operation of knife 14 onto the trimmed specimen surface 15 can thus be started.

In a preferred embodiment of the invention, a learning mode is provided for cutting device 10. In this mode, cutting device 10 can be coordinated with trimming device 12. For this purpose, a specimen 14 that has already been milled in a trimming device 12 is inserted together with specimen holder 22 into cutting device 10. Desired spacing 13 between knife 16 and the trimmed specimen surface 15 is set manually, i.e. with no automatic feed. That value is then stored in a storage device. The coordination between trimming device 12 and cutting device 10 is thereby accomplished. For each new trimmed specimen 14 that is inserted into cutting device 10 after trimming, it is then possible to travel again to exactly that spacing position after transmission of the spacing data from trimming device 12 to cutting device 10.

This learning mode can also be expanded in that several desired positions can be programmed, so that after programming the user has the ability to select one of the programmed positions to be moved to.

Provision can furthermore be made in cutting device 10, and also in trimming device 12, to move automatically to the zero position—which corresponds to a defined spacing 13 between knife 14 and specimen holder 22, and between milling cutter 17 and specimen holder 22—at each activation. A reliable measurement of the absolute distance traveled, using the distance measurement system in cutting device 10, can thus be guaranteed.

It is of course also possible to use, instead of the trimming apparatus, a separate device for measuring the spacing between specimen holder 22 and the trimmed specimen surface 15. In this case as well, however, the data must be transferred to the cutting device.

What is claimed is:

1. A method for automatically presetting and cutting a specimen with a microtome or ultramicrotome, the specimen having a trimmed surface, the method comprising the steps of:
    providing a microtome or ultramicrotome with a knife holder for a knife and a specimen holder for holding the specimen;
    using a feed device for producing a relative motion between the knife and the specimen;
    producing a trimmed surface of the specimen with a trimming apparatus having a trimming knife or a milling cutter;
    ascertaining in the trimming apparatus the spacing between the trimmed surface of the specimen and the specimen holder with a distance measurement system during the movement of the trimming knife or the milling cutter; and,
    transferring the spacing to the microtome or ultramicrotome via a data transfer means, prior to mounting the specimen with the specimen holder in the microtome or ultramicrotome.

2. The method as defined in claim 1, wherein after trimming, the specimen is inserted together with the specimen holder into the microtome or ultramicrotome and the specimen holder abuts against a stop.

3. The method as defined in claim 1, wherein the motion of the trimming knife or the milling cutter is sensed with a distance measuring system.

4. The method as defined claim 1, wherein the trimming apparatus and the microtome or ultramicrotome are coordinated with one another in a learning mode.

5. The method as defined in claim 4, comprising the steps of:
    setting a defined spacing between the trimmed surface of the specimen and the knife in the microtome or ultramicrotome; and
    storing the defined spacing.

6. The method as defined in claim 1, wherein the trimming knife or the milling cutter is equipped with a travel measurement system that has a zero mark; and
    the trimming knife or the milling cutter is moved to the zero mark upon activation of the microtome or ultramicrotome.

* * * * *